US006306150B1

United States Patent
Levinson

(10) Patent No.: US 6,306,150 B1
(45) Date of Patent: Oct. 23, 2001

(54) SURGICAL CLIPS FOR SURGICAL INSTRUMENT FOR STAPLING AND CUTTING BLOOD VESSELS AND ORGANIC STRUCTURES

(75) Inventor: Melvin E. Levinson, Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

(21) Appl. No.: 09/677,200

(22) Filed: Oct. 2, 2000

Related U.S. Application Data

(62) Division of application No. 09/235,412, filed on Jan. 22, 1999.

(51) Int. Cl.[7] ................................................ A61B 17/08
(52) U.S. Cl. ........................ 606/158; 606/151; 606/157
(58) Field of Search .................................. 606/151, 157, 606/158, 120, 221, 219, 220; 24/545–547; 227/902

(56) References Cited

U.S. PATENT DOCUMENTS

| 3,326,216 | | 6/1967 | Wood . | |
| 3,363,628 | * | 1/1968 | Wood | 606/158 |
| 3,631,707 | | 1/1972 | Miller . | |
| 3,675,688 | | 7/1972 | Bryan et al. . | |
| 3,713,533 | | 1/1973 | Reimels . | |

FOREIGN PATENT DOCUMENTS

| 0285776 | * | 10/1988 | (EP) | 606/158 |

OTHER PUBLICATIONS

Ethicon Endo–Surgery Tool Product Spec. Sheets, circa 1998 Richard Wolf Product Brochure, p. 1, circa.
Storz Sinus Instrument Product Brochure, circa 1998.
Circon Reposable Laparoscopic Instrument Product Spec. Sheets pp. 205, 208, cir. 9 Snowden–Pencer Endoscopic Plastic Surgery Product Spec., p. 5, circa 1998.
CIT GmbH ad for Endoscopic Instrument, circa 1998.
Scion Surgical Instrument, circa 1998 Scion Endoscope and Instrument Brochures, circa 1998.

*Primary Examiner*—Glenn K Dawson
(74) *Attorney, Agent, or Firm*—Robert C. Kain, Jr.; Fleit Kain

(57) ABSTRACT

The surgical instrument for stapling and cutting a blood vessel or other organic structure utilizes surgical staple clips. The surgical instrument includes an elongated tube or rod having a longitudinally movable rod disposed therein. A handle is mounted on the proximal end of the tube. The handle has a movable member which causes the movable rod to longitudinally shift positions in the tube. In one version, a pair of surgical staple clip-carrying jaw sets are pivotally mounted on a common lateral axis located at the distal end of the elongated tube. A scissor jaw set may also be included in the system. When the rod longitudinally moves with respect to the elongated tube or rod, the clip jaw sets clip the surgical staple clips onto the blood vessel or other organic structure. The handle for the surgical instrument includes a movable member coupled to a movable rod and a stationary grip member mounted to the elongated tube, within which moves the longitudinally movable rod. The movable handle member pivots towards and away from the stationary handle member. The movable member includes a tactile response surface which abuts a response wall on the stationary member. A surgical staple clip includes a clip face adapted to interface with the blood vessel or other organic structure. The clip face has planar facial segments and a longitudinal center channel. The longitudinal center channel has a triangular cross-section. The clip face includes terminal planar facial segments which further define X-shaped channels with vertices coextensive with the longitudinal center channel.

4 Claims, 10 Drawing Sheets

U.S. PATENT DOCUMENTS

| | | |
|---|---|---|
| 3,777,538 | 12/1973 | Weatherly et al. . |
| 3,867,944 | 2/1975 | Samuels . |
| 4,076,120 | 2/1978 | Carrol et al. . |
| 4,146,130 | 3/1979 | Samuels et al. . |
| 4,188,953 | 2/1980 | Klieman et al. . |
| 4,449,530 | 5/1984 | Bendel et al. . |
| 4,602,629 | 7/1986 | Schnirman . |
| 4,696,396 | 9/1987 | Samuels . |
| 4,844,066 | 7/1989 | Stein . |
| 4,971,198 | 11/1990 | Mericle . |
| 5,049,152 | 9/1991 | Simon et al. .................... 602/143 |
| 5,104,394 | 4/1992 | Knoepfler ........................ 606/143 |
| 5,171,250 | 12/1992 | Yoon ................................ 606/142 |
| 5,192,288 | 3/1993 | Thompson et al. ................. 60/143 |
| 5,269,792 | 12/1993 | Kovac et al. ..................... 606/158 |
| 5,336,229 | 8/1994 | Noda ................................ 606/144 |
| 5,447,513 | 9/1995 | Davison et al. .................. 606/143 |
| 5,509,920 * | 4/1996 | Phillips et al. ................... 606/157 |
| 5,514,149 | 5/1996 | Green et al. ...................... 606/158 |
| 5,713,911 * | 2/1998 | Racenet et al. ................... 606/157 |
| 5,797,922 | 8/1998 | Hessel et al. ..................... 606/120 |
| 6,217,590 * | 4/2001 | Levinson .......................... 606/142 |

\* cited by examiner

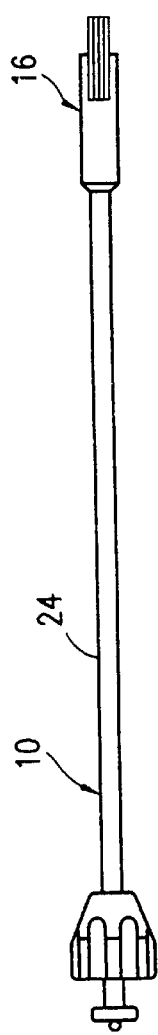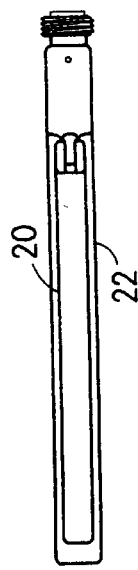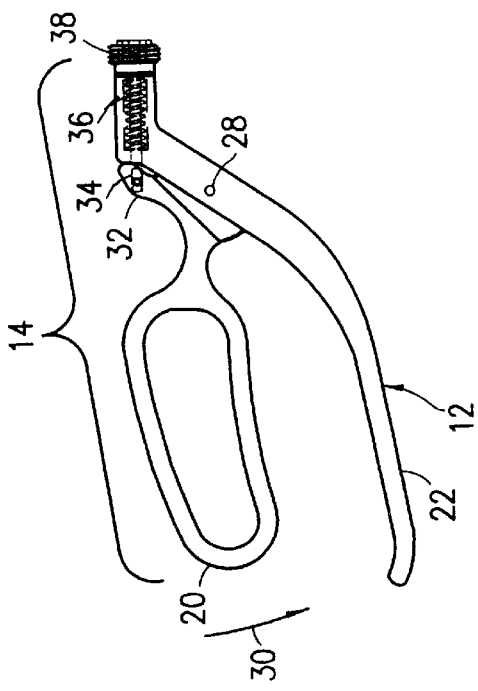

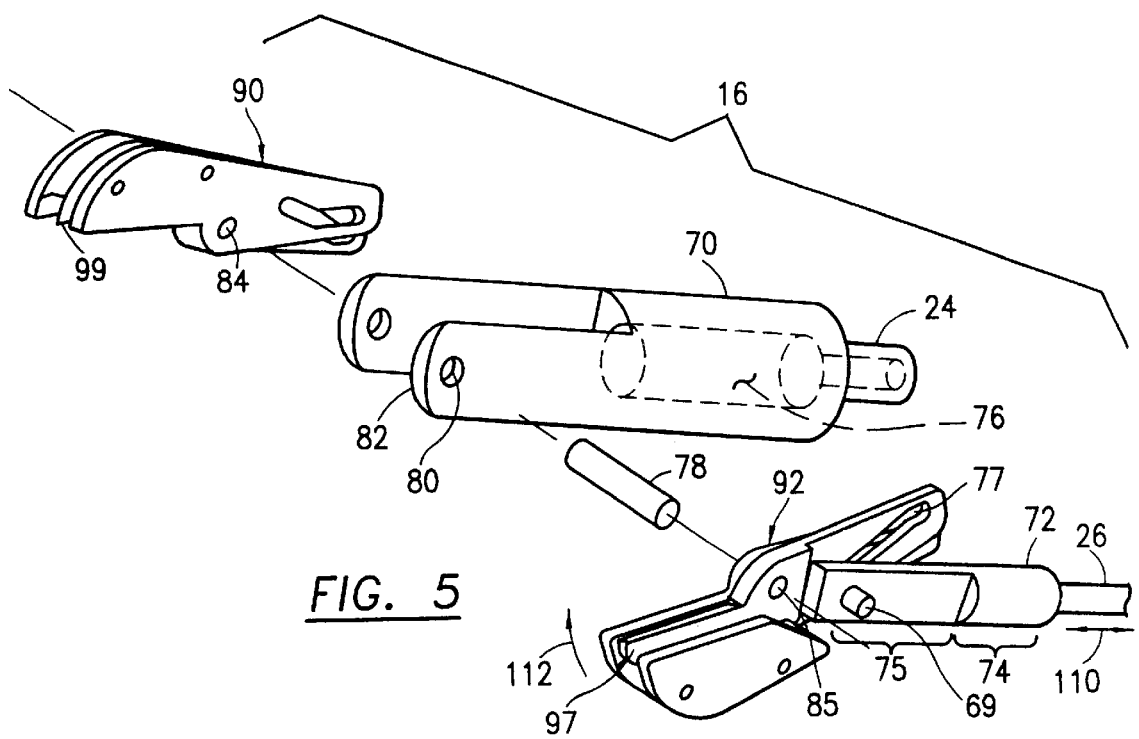
FIG. 5
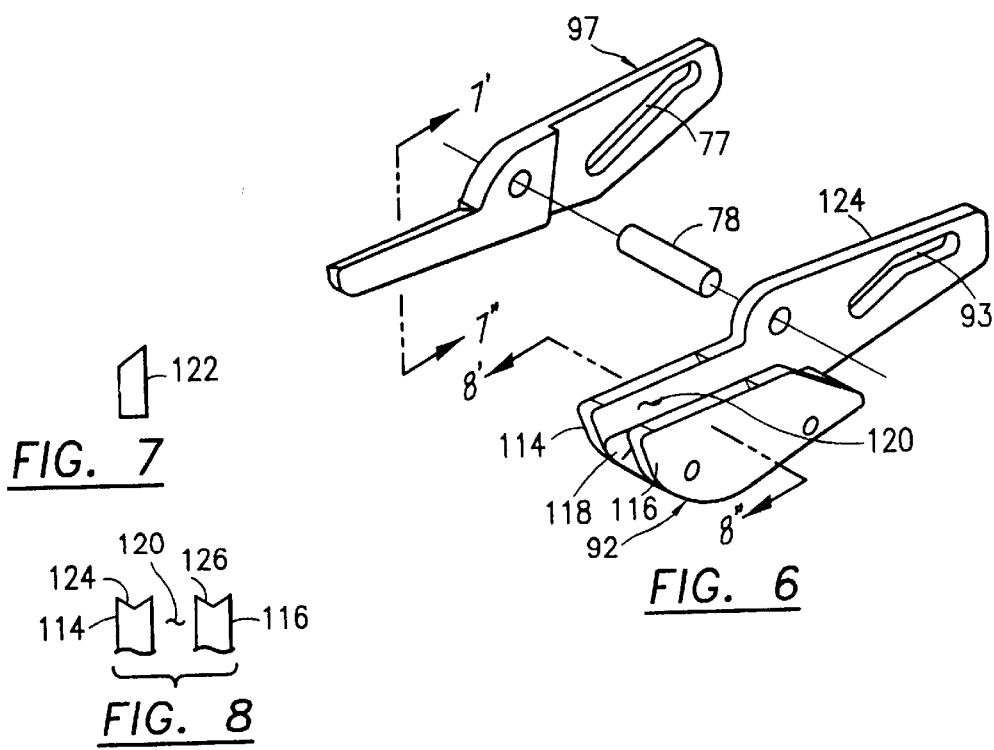
FIG. 7
FIG. 8
FIG. 6

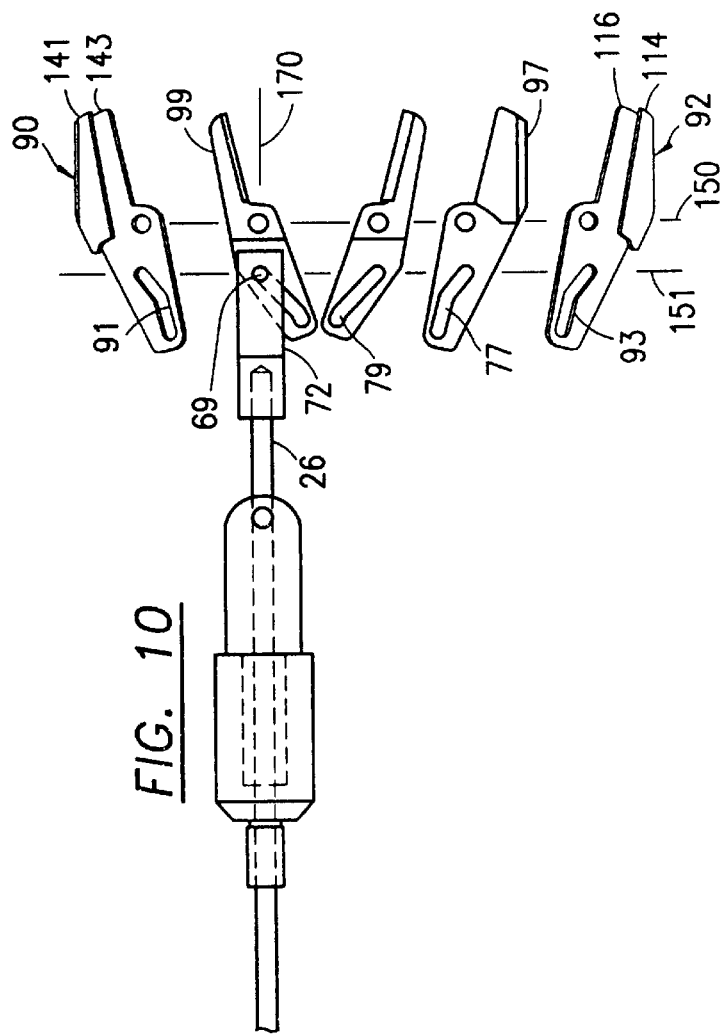
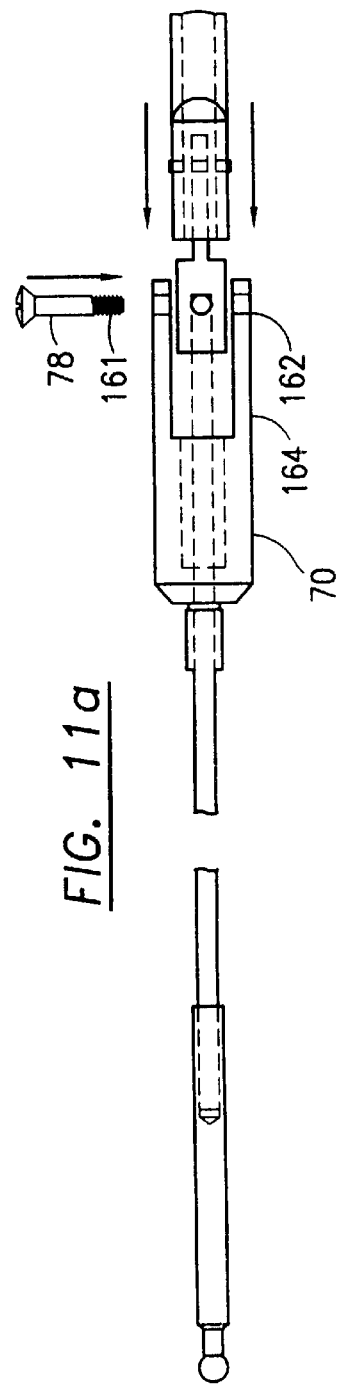
FIG. 10
FIG. 11a

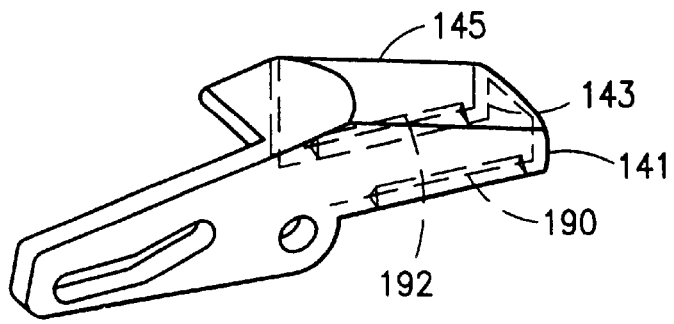
FIG. 16
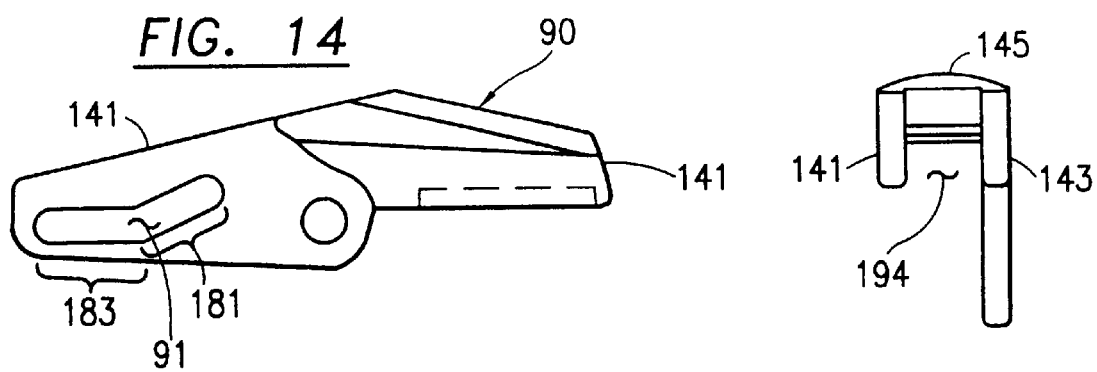
FIG. 14
FIG. 15
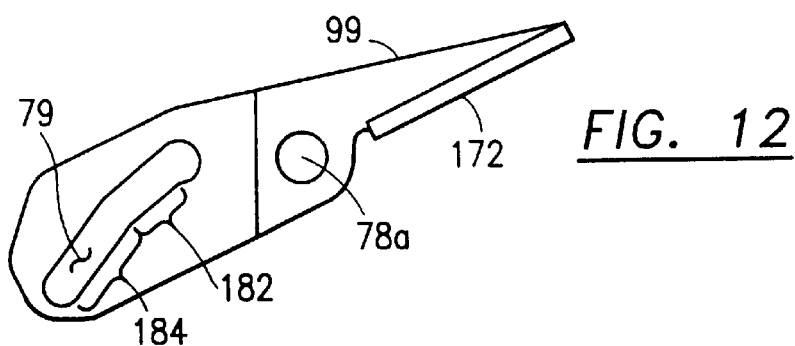
FIG. 12
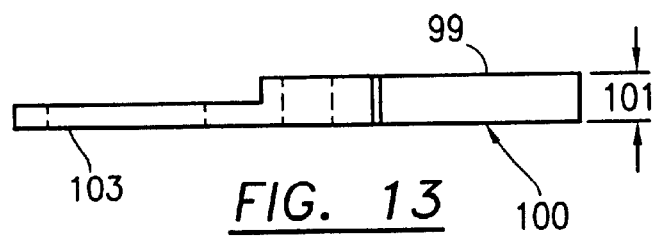
FIG. 13

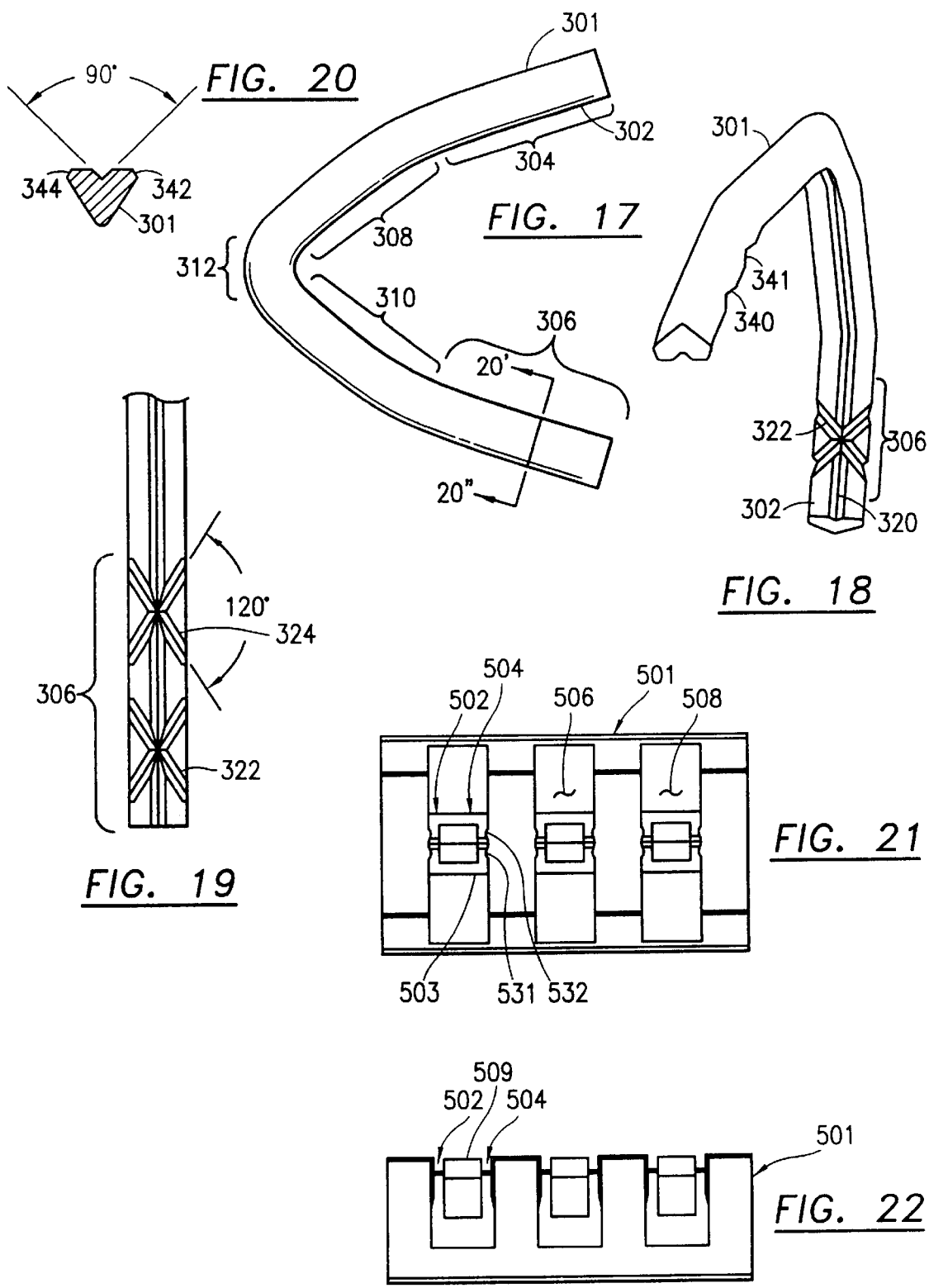

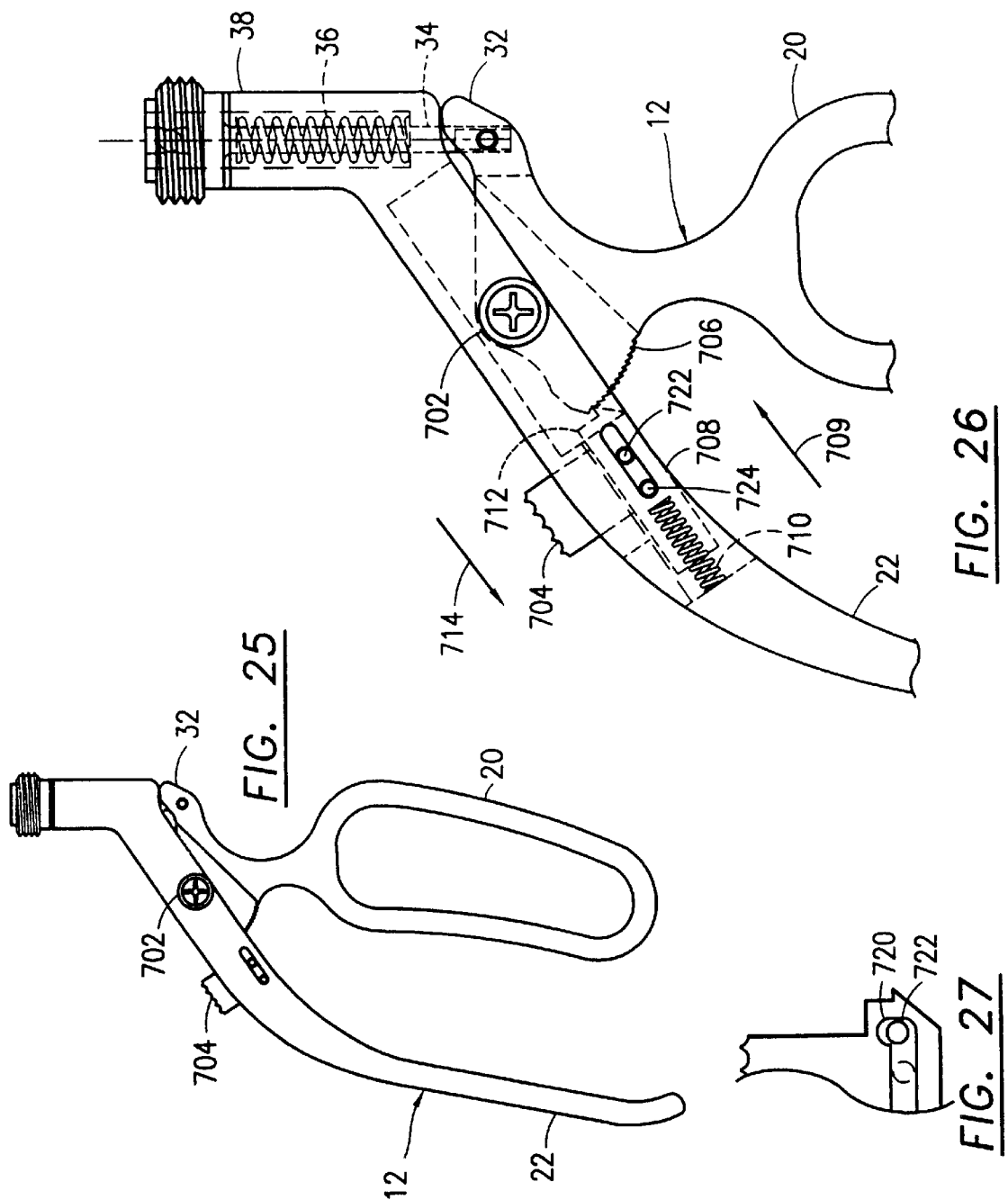

SURGICAL CLIPS FOR SURGICAL INSTRUMENT FOR STAPLING AND CUTTING BLOOD VESSELS AND ORGANIC STRUCTURES

This is a divisional patent application based upon U.S. patent application Ser. No. 09/235,412, filed Jan. 22, 1999, now pending.

The present invention relates to a surgical instrument for stapling and cutting a blood vessel or other organic structure, a method for stapling and cutting, surgical staple clips designed to grip the blood vessel or other organic structure, and a handle for the surgical instrument.

BACKGROUND OF THE INVENTION

The following patent references show surgical instruments having various features. U.S. Pat. No. 3,675,688 to Bryan describes a surgical tool for ligating, suturing and dividing organic tubular structures in a single unitary operator movement by first capturing the tubular structure in a jaw subassembly which encompasses both the forward exposed side of the tubular structure and the opposing, rearward side of the tubular structure (FIG. 11a, jaw size beta). Thereafter in a single operator stroke, a rod moves rearward with respect to the distal end of the instrument, ligating the organic structure, then firing a pair of staples over the structure (ejecting the staples with a spring force) and cutting the tubular structure with a knife intermediate the staples.

U.S. Pat. No. 3,777,538 to Weatherly discloses a surgical device which applies a singular clip to ligate an organic tubular structure.

U.S. Pat. No. 4,602,629 to Schnirman discloses a combined surgical blade and clip assembly including a pair of opposing platforms, joined together by a spring hinge. The platforms have multiple platform levels. The lowest levels hold clips which, upon depression of the hinge and compression of the low level platform surfaces together, clips legs closed about the tubular organic structure. Thereafter upon further compression of the hinge and opposing platforms, the pair of opposing high level platform surfaces move towards each other. A blade is mounted on at least one high level platform. Upon compression of the high level platforms, the blade cuts the tubular structure. The opposing high level platform has an anvil or a blade sheath to guide the blade. The blade and clip assembly is carried in the jaws of a surgical clamp. The clips, carried on the lower platform levels, are dispensed on the tubular structure and remain thereon after the tube is cut. U.S. Pat. No. 5,104,394 to Knoepfler discloses an automatic stapler which staples or clips and then cuts an organic tubular structure. Upon compression of the operator's handle,jaws carrying a staple clip close at the distal end of the device. If the operator wants to cut an item at the stapled site, he or she moves a thumb slide, located at a remote location on the handle, away from the compressible hand grip. The system dispenses a single staple clip during each operation. U.S. Pat. No. 5,336,229 to Noda discloses a dual stapler or ligating assembly with a surgical blade. In operation, the operator depresses a compressible handle and then depresses a separate trigger to transect the organic tissue. U.S. Pat. No. 5,447,513 to Davison discloses a stapler and surgical blade assembly having a single staplerjaw pair, a blade and blade guide subassembly, angularly displaced with respect to each other at the distal end of the stapler-blade assembly. See FIG. 3. To staple and cut the blood vessel, the operator staples one location on the vessel, moves the distal end of the instrument along the vessel to a second location, dispenses another staple and then maneuvers the blade slide, on the instrument's handle, and cuts the vessel at an intermediate position.

U.S. Pat. No. 3,631,707 to Miller discloses a hemostatic clamp carrying a surgical staple or clip for blood vessels.

The following patent reference shows a surgical handle design: U.S. Pat. No. 5,171,250 to Yoon discloses a handle which the operator must compress to close and dispense a staple clip on an anatomical structure. Prior to compressing the handle, the operator squeezes a trigger then rotates a pivoting lock bar away from the compressible handle. After dispensing the staple, the operator depresses a second compressible handle located at a proximal end above the primary compressible handle.

The following patent references show various clip grip patterns for surgical staples or clips: U.S. Pat. No. 5,192,288 to Thompson discloses in FIG. 11aB a surgical clip with a shallow, longitudinal grove (having a truncated, conical cross-section) and V-shaped cross channels. The vertex of the V channels is directed towards the vertex of the staple clip. U.S. Pat. No. 5,269,792 to Kovac discloses surgical clips in FIGS. 13A, B and C with a longitudinal channel (having a pentagonal, cross-sectional shape) and laterally disposed V channels (also pentagonal). The V channels have vertices directed away from the primary vertex of the staple clip.

U.S. Pat. No. 3,326,216 to Wood shows a large, central channel and cross or lateral channels having an equal depth. U.S. Pat. No. 3,867,944 to Samuels shows longitudinally disposed, peripherally located, protrusions. U.S. Pat. No. 4,188,953 to Klieman shows a clip with flat surface and diagonal channels. U.S. Pat. No. 4,449,530 to Bendel shows a clip with a cross-hatch active surface. U.S. Pat. No. 4,696,396 to Samuels shows clips with centrally aligned protrusions. U.S. Pat. No. 4,844,066 to Stein shows clips with a central, longitudinal channel and lateral cross channels. The longitudinal channel is generally rectilinear. Stein's clip first deforms the fore-ends of clip legs, then closes about tubular organic structure. U.S. Pat. No. 4,971,198 to Mericle shows, in FIG. 6, a clip with a shallow, longitudinal channel and deep cross or lateral channels. The lateral channels are square and deep.

The following patent references show various surgical clips or staple holders: U.S. Pat. No. 3,713,533 to Reimels; U.S. Pat. No. 4,076,120 to Carroll; and U.S. Pat. No. 4,146,130 to Samuels.

OBJECTS OF THE INVENTION

It is an object of the present invention to provide a surgical instrument for stapling and cutting a blood vessel or other organic structure in a singular, operative stroke. As used herein the term "blood vessel" refers to any anatomical, tubular structure in a mammal. The term "organic structure" refers to any anatomical structure in a human or other mammal. Sometimes the term "blood vessel" is used as a shorthand reference to both "blood vessels" and "organic structures."

It is another object of the present invention to provide a method for surgically stapling and cutting a blood vessel or other organic structure in a body by simultaneously clipping both sides of a segment of a blood vessel (or other organic structure) and then, in the same, singular, operative stroke, cutting the segment wherein the clipping occurs during an initial portion of the stroke and the cutting occurs during a subsequent portion of the stroke.

It is an additional object of the present invention to provide surgical clips having unique, non-slip, high traction pattern to clamp or clip a blood vessel or other organic structure in the body.

It is an additional object of the present invention to provide a surgical instrument wherein a pair of surgical staple clips are first clamped onto the blood vessel or other organic structure in the body and then, during the single, operative stroke, the blood vessel or organic structure is cut.

It is an another object of the present invention to provide a surgical instrument with clip jaw sets and a scissor jaw set which are actuated at different times based on a single stroke of a cam moving in dissimilar cam follower channels.

It is an additional object of the present invention to provide a surgical instrument wherein a cam pin is retracted and the clip jaw sets first close on the blood vessel and, immediately thereafter, the scissor jaw set cuts the blood vessel or organic structure based upon further retraction of the cam pin. The cam pin moves in the clip-action cam follower channel and the cut-action cam follower channel.

It is an additional object of the present invention to provide a surgical instrument with a compressible handle that retracts a rod carrying the cam pin at the distal end of the rod.

It is another object of the present invention to pivotally mount the clip jaw sets and the scissor jaw set on a common lateral axis at the distal end of an elongated tube within which longitudinally moves an actuator rod.

It is another object of the present invention to provide a method for surgically stapling and cutting a segment of a blood vessel or other organic structure utilizing a retracting rod to simultaneously clip both sides of the blood vessel segment (or other organic structure segment) and then cut the segment during a singular, operative stroke and rod retraction.

It is a further object of the present invention to provide a method utilizing two U-shaped surgical staple clips and simultaneously collapsing both U-shaped clips onto the blood vessel or organic structure segment.

It is another object of the present invention to provide a method wherein the clipping and cutting steps include the step of translating the singular rod retraction into sequential pivotal movement about a common axis at the distal end of the surgical instrument.

It is another object of the present invention to provide a handle for a surgical instrument.

It is a further object of the present invention to provide a handle with a movable handle member having a tactile response surface which abuts a response wall on a stationary handle member.

It is a further object of the present invention to provide the tactical response surface which informs the operator, via tactile sensations, that he or she has moved the handle and has retracted or extended the rod through certain discrete segments thereby signaling to operator that the surgical instrument has clipped and, subsequently, cut the blood vessel or organic structure.

It is another object of the present invention to provide various tactile response surfaces on the movable handle member and different tactile response walls on the stationary handle member.

It is an additional object of the present invention to provide a latch or a ratchet lock on the handle.

It is another object of the present invention to provide a surgical staple clip for use with the surgical instrument.

It is a further object of the present invention to provide a surgical staple clip having a longitudinal center channel on a clip face and X-shaped channels with vertices coextensive with the longitudinal center channel to provide a high degree of traction on the clip face.

It is an additional object of the present invention to provide a surgical staple clip wherein two X-shaped channels are defined on terminal planer facial segments of the clip face.

SUMMARY OF THE INVENTION

The surgical instrument for stapling and cutting a blood vessel or other organic structure utilizes surgical staple clips. The surgical instrument includes an elongated tube having a longitudinally movable rod disposed therein. A handle is mounted on the proximal end of the tube. The handle has a movable member which causes the movable rod to longitudinally shift positions in the tube. A pair of surgical staple clip-carrying jaw sets are pivotally mounted on a common lateral axis located at the distal end of the elongated tube. Each clip jaw set includes two jaw members. Each jaw member defines a clip channel at its jaw mouth. The surgical clips reside in the clip channels when the surgical instrument is utilized. A scissor jaw set is disposed intermediate the pair of clip jaw sets and is also pivotally disposed on the same common lateral axis. The surgical instrument includes a laterally extending cam that is mounted on the distal end of the movable rod. The cam, preferably a laterally extending pin, moves within cam follower channels defined in the clip jaw sets and the scissor jaw set. Accordingly, each clip jaw set defines a clip-action cam follower channel and the scissor jaw set defines a cut-action cam follower channel. When the cam moves based upon the longitudinal movement of the rod, the clip jaw sets first clip the blood vessel or other organic structure due to the clip-action cam follower channels. Thereafter, the scissor jaw set closes based upon the longitudinal movement of the cam in the cut-action cam follower channel.

To achieve the sequential clip and then cut-action, the clip-action cam follower channels define different, non-linear channel segments as compared to the cut-action cam follower channel. In a preferred embodiment, the movable rod retracts the cam from the distal end of the elongate tube.

The method for stapling and cutting a blood vessel or other organic structure utilizes an elongated surgical instrument carrying two surgical staple clips at the distal end of the surgical instrument. The method includes the steps of providing a movable rod, coextensive with the elongated surgical instrument, extending from an outboard, proximal position to a distal, surgical site in the body. The method also includes providing two surgical staple clips at the distal end of the rod. The method involves axially retracting said rod in a single, operative stroke, simultaneously clipping both sides of the designated segment of blood vessel or other organic structure with the two surgical staple clips during an initial portion of the stroke, and subsequently cutting the segment or other organic structure during a subsequent portion of the singular, operative stroke. In a preferred embodiment, the method includes simultaneously collapsing U-shaped clips onto the segment. The clipping and subsequent cutting is provided, in a further embodiment, by a singular operative stroke caused by a single, generally uniform, retraction of the rod away from the distal end of the surgical instrument. The clipping and cutting includes, in an enhanced embodiment, the step of translating the singular rod retraction movement into sequential, pivotal movement about a common axis at the distal end of the surgical instrument.

In another embodiment, a handle for a surgical instrument is provided. The handle includes a movable member coupled to a movable rod in an elongated surgical instrument. The handle also includes a stationary grip member mounted to the elongated tube, within which moves the longitudinally movable rod. The movable handle member pivots towards and away from the stationary handle member. The movable member includes a tactile response surface which abuts a response wall on the stationary member. The tactile response surface generates tactile responses to the operator when the movable member pivots towards the stationary member due to interference with the tactile response wall. In one embodiment, the tactile response surface on the movable handle member is an undulated or wavy surface which rides over a generally planar tactile response wall. In another embodiment, the tactile response surface defines a plurality of ridges which ride over a generally planar or other specially shaped tactile response wall. In a further embodiment, the tactile response surface defines a plurality of fine tooth ridges and the tactile response wall includes a complementary, biased fine tooth providing tactile responses upon movement of the movable handle member relative to the stationary handle member.

In a further embodiment of the handle, the tactile response surface and the responsive tactile piece define a ratchet or a latch set. A responsive tactile piece is carried by the stationary handle member and generates tactile responses to the operator when the tactile response surface on the movable handle member translates or moves past the responsive tactile piece. In a further embodiment, the responsive tactile piece is biased towards the tactile response surface. Further, the responsive tactile piece includes an operator control surface to provide a counter force against the biased member which is part of the responsive tactile piece. In other words, the operator moves the biased member by placement of an appropriate force on the control surface against the biasing force which generally directs the biased member towards the tactile response surface on the movable handle member. In a further embodiment, the biased member can be latched in place with respect to the stationary handle member with a latch. In one embodiment, the latch includes a detent and a complementary nub.

The surgical staple clip is utilized for closure of a blood vessel or other organic structure. The surgical staple clip includes a clip face adapted to interface with the blood vessel or other organic structure. The clip face has planar facial segments and a longitudinal center channel. The longitudinal center channel has a triangular cross-section. The clip face includes terminal planar facial segments which further define X-shaped channels with vertices coextensive with the longitudinal center channel. The X-shaped channels also have a triangular cross-section. In a further embodiment, the surgical staple clip includes two X-shaped channels on each terminal planar facial segment.

BRIEF DESCRIPTION OF THE DRAWINGS

Further objects and advantages of the present invention can be found in the detailed description of the preferred embodiments when taken in conjunction with the accompanying drawings in which:

FIG. 3 diagramatically illustrates a cross-section of the surgical instrument from the perspective of section line 3'-3" in FIG. 1;

FIG. 5 diagramatically illustrates an exploded view of the end piece showing one clip jaw set and an upper scissor jaw member, the common lateral axis, the distal end of the elongated tube, the other clip jaw set and lower scissor jaw member and the distal end of the movable rod;

FIG. 6 diagramatically illustrates an exploded view of one clip jaw set and the lower scissor jaw member;

FIGS. 7 and 8 diagramatically illustrate cross-sectional views of the blade of the scissor jaw member and the clip carrying channels of the clip jaw members from the perspective of section lines 7'-7" and 8'-8" in FIG. 6;

FIG. 10 diagramatically illustrates an exploded view of the pair of clip jaw sets, the scissor jaw set, the movable rod and the distal end of the elongated tube;

FIG. 11a diagramatically illustrates a top view of an exploded, partially assembled surgical instrument and the common axis pin for the end piece;

FIGS. 12 and 13 diagramatically illustrate a side view and a top view of the scissor jaw member, respectively;

FIGS. 14, 15 and 16 diagramatically illustrate a side view, an end view and perspective view of a clip jaw member, respectively;

FIG. 17 diagramatically illustrates a side view of a surgical clip;

FIG. 18 diagramatically illustrates a perspective view of the surgical clip showing the X-shaped channel on the terminal, planar facial segment and the longitudinal center channel;

FIG. 19 diagramatically illustrates the surgical clip with two X-shaped channels on the terminal planar facial segment;

FIG. 20 diagramatically illustrates a cross-section of the clip from the perspective of section line 20'-20" in FIG. 17;

FIGS. 21 and 22 diagramatically illustrate a top view and a side view of the surgical staple clip holder;

FIG. 25 diagramatically illustrates a side view of the handle for the surgical instrument with a latch or a ratchet mechanism and the protruding operator control surface;

FIG. 26 diagramatically illustrates a detailed view of the responsive tactile piece, the biased member, fine-tooth ridges on the tactile response surface and the operator control surface; and, FIG. 27 diagramatically illustrates the latch for the biased member with a detent and complementary nub to latch the biased member away from the tactile response surface on the movable handle member.

DETAILED DESCRIPTION OF THE PREFERRED EMBODIMENTS

The present invention relates to a surgical instrument for stapling and cutting a blood vessel or other organic structure in a body, a method for surgically stapling and cutting, a handle for a surgical instrument and a surgical staple clip.

FIGS. 1–16 generally diagramatically illustrate preferred embodiments of the surgical instrument. FIGS. 17–20 generally diagramatically illustrate the surgical clip. FIGS. 21 and 22 generally diagramatically illustrate the clip holder. FIGS. 23–27 diagramatically illustrate several handle configurations for the previously discussed surgical instrument or other surgical instruments wherein an axially movable rod actuates a surgical mechanism at a distal end of the instrument.

Figures 1, 11B:
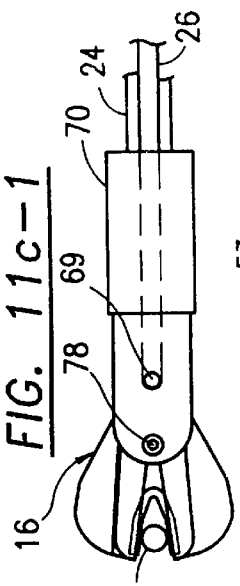
FIG. 1 diagramatically illustrates a side-elevational view of the surgical instrument.
FIGS. 11b through 11e diagrammatically illustrate the method which clips segment A of a blood vessel and then cuts the blood vessel or other organic structure.
Figures 2, 11B:
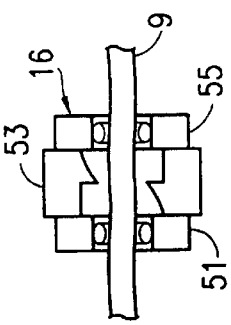
FIG. 2 diagramatically illustrates a top view of the surgical instrument.

FIG. 1 generally diagramatically illustrates surgical instrument 10 having a handle 12 at its proximal end 14 and an end piece 16 at its distal end 18. End piece 16 is the surgical mechanism operated by the handle in the embodiment shown in FIGS. 1 and 2. FIG. 2 diagramatically illustrates a top view and particularly shows movable handle member 20 disposed generally above stationary handle member 22. Surgical instrument 10 includes an elongated tube 24 and a movable rod 26 disposed within tube 24. FIG. 3 diagramatically illustrates a cross-sectional view of instrument 10 and particularly rod 26 disposed within elongated tube 24. In a working embodiment, tube 24 closely encapsulates rod 26.

With respect to handle 12, movable handle member 20 is pivotally attached at pivot point 28 to stationary handle member 22. Movable handle member 20 moves in the direction shown by arrow 30 when the operator compresses the handle. Stem 32, at a point beyond pivot 28, is attached to actuator rod 34. Handle 20 is biased to an outboard position (shown in FIG. 1) by spring 36. Further details of handle 12 are shown and discussed later in conjunction with FIGS. 23–27. Only certain operational items are discussed with respect to FIG. 1.

The inboard portion of handle 12 terminates in a male threaded joint 38. Actuator rod 34 terminates in a female coupler (not shown in FIG. 1) which mates with male coupler piece 40 at the proximal end of movable rod 26. This mechanical coupling system is shown in detail later in connection with FIG. 24. It should be noted that the male and female couplers may be transposed such that movable rod 26 terminates in a female coupler. A female coupling unit 42 (illustrated in FIG. 1) slides over rod 26 as shown by double headed arrow 44. Also, as discussed later in connection with FIG. 24, female coupler unit 42 has female threads and a freely rotatable outer unit such that when female coupler is rotated as shown by double headed arrow 46, the elongated tube 24 rotates thereby rotating end piece 16.

Figure 4:
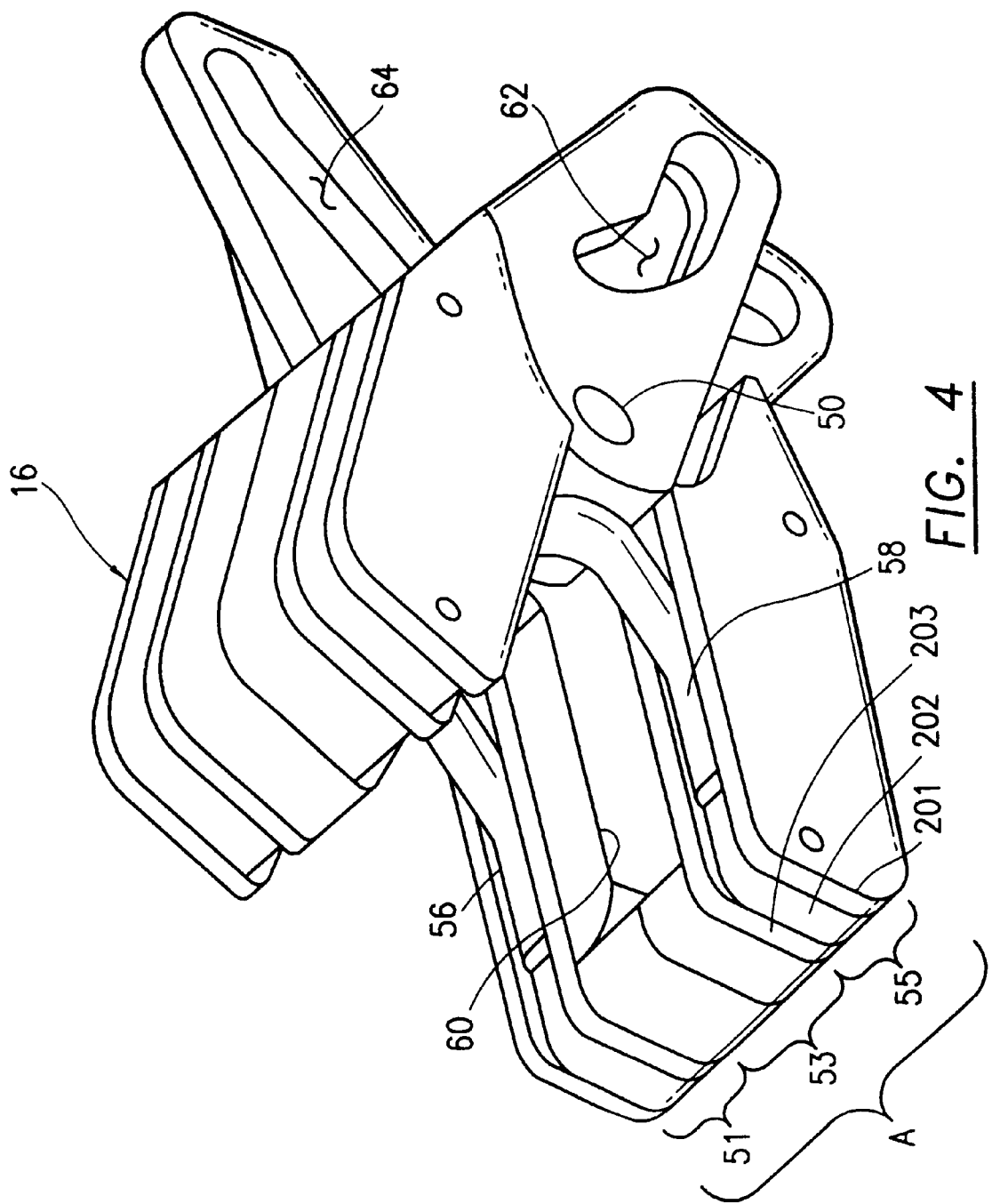
FIG. 4 diagramatically illustrates a perspective view of the end piece for the surgical instrument showing the clip jaw sets and the scissor jaw set.

FIG. 4 is a diagrammatic, perspective view of end piece 16. As described in detail hereinafter, end piece 16 includes a plurality of pivoting members, all of which pivot about a common lateral axis 50, One of these members is a clip jaw member generally designated at lateral jaw area 51, a scissor jaw member, generally designated at lateral jaw area 53 and another clip jaw member generally designated at lateral jaw area 55. The clip jaw sets carry surgical clips 56 and 58. The scissor jaw set carries scissor blades, one of which is scissor blade 60 in the lower portion of the jaw mouth. As described in detail hereinafter, the clip jaw sets initially close based on the two-part, linear configuration of clip-action cam follower channels, one of which is cam follower channel 62. Thereafter, the scissor jaw set closes based upon the two-part, linear configuration of the cut-action cam follower channel generally designated as channel 64.

FIG. 5 diagramatically illustrates an exploded view of end piece 16. The elements in FIG. 5 are not shown in sequential assembly order. Elongated tube 24 terminates in end member 70. Movable rod 26 terminates in rod end piece 72. Rod end piece 72, and particularly inboard segment 74 (inboard or close to rod 26), moves longitudinally in cavity 76 of end member 70. The two clip jaw sets and scissor jaw set pivot about a common lateral axis established by pin or bolt 78. Pin 78 passes through holes or apertures, one of which is aperture 80 at the outboard end 82 of end member 70. Pin 78 also passes through hole or aperture 84 and jaw member 90. Pin 78 also passes through an aperture in jaw set 92. Further, pin 78 passes through aperture or hole 85 in scissor jaw member 97.

A laterally extending cam 69 extends laterally from an outboard region 75 of rod end member 72. The term "laterally" refers to a position or direction generally normal (perpendicular) to rod 26 and tube 24. As explained later in great detail, since the jaw sets 90, 92 and the scissor jaw members 97,99 all pivot about a common lateral axis (defined by pin 78), when rod 26 moves longitudinally (as shown by double headed arrow 110), cam 69 moves in the cam follower channels established at the inboard plate segments of the jaw sets 90, 92 and scissor jaw members 97, 99. For example, scissor jaw member 97 includes a cut-action cam follower channel 77. When cam 69 moves in the direction shown by arrow 10 (to the right in FIG. 5, a retracting motion), jaw member 97 moves upward as shown by arrow 112 due to cam 69 moving to the right and in cut-action cam follower channel 77. This is described in greater detail in later figures.

FIG. 6 diagramatically illustrates scissor jaw member 97, pin 78 establishing the common lateral axis and clip jaw set 92. Clip jaw set 92 includes a first and a second jaw member 114, 116, joined together by a base plate 118. A space 120 is defined between jaw members 114, 116. A cutting blade 122 for scissor jaw member 97 is disposed in space 120.

Jaw set 92, in the illustrated embodiment, defines the lower jaw mouth for end piece 16. Jaw member 114 is a plate which includes or defines a back plate 124. Back plate 124 is inboard with respect to pin 78 defining the common axis and is also inboard with respect to the jaw mouth fore end piece 16. The inboard back plate 124 defines a clip-action cam follower channel 93. Cam 69 is disposed in cam follower channel 93. As used throughout this specification, the term "clip" refers to a surgical staple clip rather than an action which "cuts." Hence, "clip-action" refers to collapsing a surgical staple clip onto a blood vessel or other organic structure in a body.

Scissor jaw member 97 includes a back plate with a cut-action cam follower channel 77 within which moves cam 69.

As shown in FIG. 6, cam 69, when moving in clip-action cam follower channel 93 will close jaw plates 114, 116 at a time prior to the closure of scissor blade 122 of scissor jaw member 97. The closure of clip jaw set 92 prior to the closure of scissor jaw member 97 is due to the fact that clip-action cam follower channel 93 has a greater angular offset, offset from the instrument's axial center line, as compared with the angular offset for cut-action cam follower channel 77. The comparatively greater angular offset of the clip-action follower channel in the first or initial linear channel segment causes the clips to close before the scissor jaws close.

FIG. 7 diagramatically illustrates a cross-section of the blade on the scissor jaw member blade portion 122. FIG. 7 is viewed from the perspective of section line 7'–7" in FIG. 6.

FIG. 8 diagramatically illustrates the cross-sectional view of clip retention channels 124, 126 on jaw set members or plates 114, 116. Other clip retaining channels may be provided on clip plates 114, 116. As stated earlier, scissor blade 122 moves within space 120 intermediate jaw plates 114, 116. Accordingly, base plate 118 (connecting jaw plates 114, 116) protects the radial backside of the scissor blades. This base plate 118 may prevent fouling of the blades during the surgical procedure.

Figure 9:
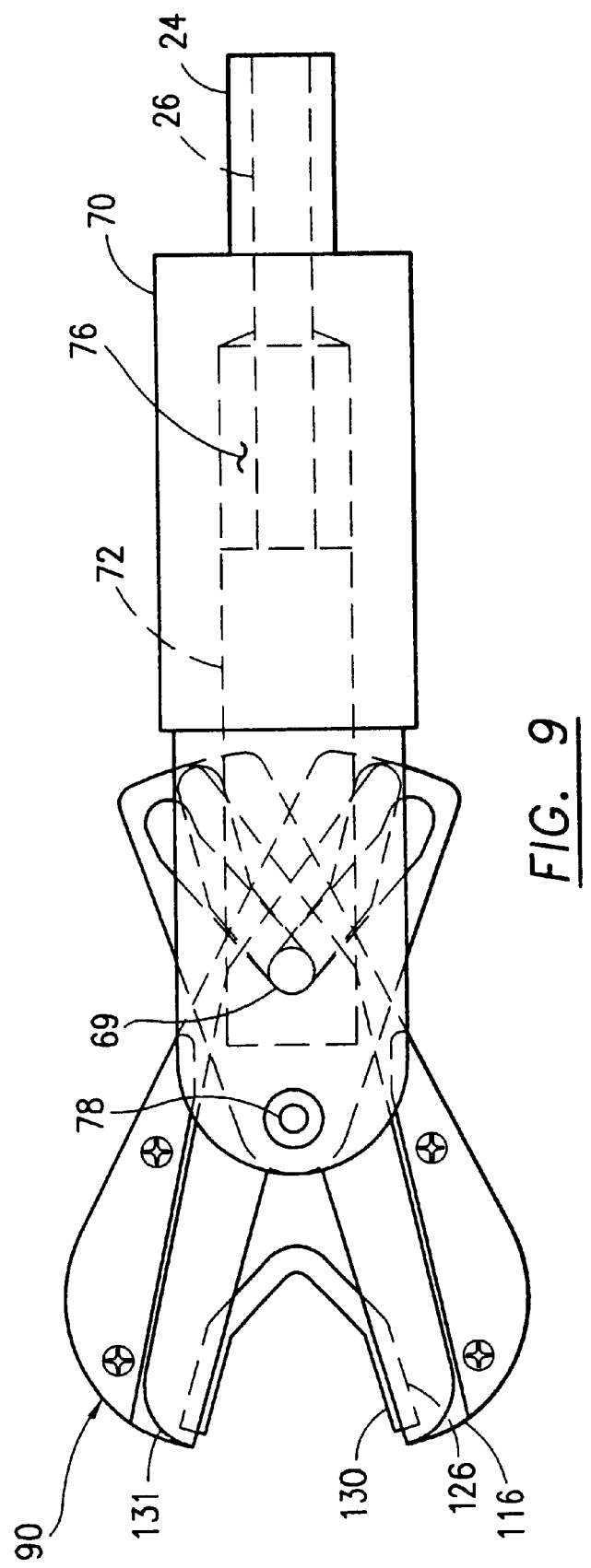
FIG. 9 diagramatically illustrates the end piece and various cam follower channels, the distal end of the elongated tube and the distal end of the movable rod.

FIG. 9 diagramatically illustrates movable rod 26 closely captured and retained in elongated tube 24. Rod end member 72 is shown movably disposed within space 76 of tube end member 70. The clip jaw sets and scissor jaw set pivot about pin 78. Cam 69 moves within the aforementioned cam follower channels. Jaw plate 116 retains clip 130 in clip channel 126. The generally U-shaped clip 130 has a leg which is captured by jaw plate 131 of clip jaw set 90. The cam follower channels are also illustrated in FIG. 9.

In FIG. 9, the clip-action and cut-action cam follower channels have the same initial or leading angular offset (with respect to the axial center line of rod 26); however, the length of the cut-action initial or leading channel segment is longer than the initial channel segments of the clip-action cam follower channels. In this manner, the clips are collapsed or "clipped-on" the blood vessel and then the scissor blades are forced to close further (e.g., causing on lower blade edge 122 (FIG. 6) to bypass the upper blade edge) to ensure that the blood vessel or other organic structure of the surgical site is cut or completely severed. As used herein, reference to "a blood vessel" also includes the concept of clipping and cutting an organic structure at a surgical site in a mammal.

FIG. 10 diagramatically illustrates an exploded view of the surgical end piece and shows the two clip jaw sets 90, 92 and the scissor jaw set which includes scissor jaw members 97, 99. Lower clip jaw set 92 includes jaw plates 114, 116 (see FIG. 6). Clip jaw set 90 includes jaw plates 141, 143. A single surgical clip (not shown) resides in the clip channels of jaw plates 114, 141. This is generally shown as lateral jaw region 55 in FIG. 4 which shows a perspective view of end piece 16. The clip channels for jaw plates 116, 143 retain clip 56 as shown in lateral jaw area 51 of FIG. 4. Scissor jaw members 97, 99 together form a scissor jaw set. The clip jaw sets 90, 92 and the scissor jaw set, collectively a single set formed by members 97, 99, all pivot about a common lateral axis illustrated as axis 150 in FIG. 10. Cam 69, which extends laterally from rod end piece 72, extends into cam follower channels 93, 77, 79, 91. All the cam follower channels define non-linear, two-part channel segments in the illustrated embodiment. Although clip-action cam follower channels 93, 91 are mirror images of each other thereby coordinating the closure of jaw plates 141 and 114 (left clip), 143 and 116 (right clip), the cut-action cam follower channels 77, 79 for the scissor jaw set 97, 99 establish different cam actions compared to the clip-action channels. Accordingly, jaw sets 90, 92 first close and then, at a subsequent time, scissor jaw members 97, 99 close FIG. 11a diagrammatically illustrates pivot pin 78 having a male threaded portion 161 which threadably mounts to females threads 162 on outboard extending prong 164 of tube end member 70.

Although rod 26 is shown as closing the clip jaw sets and then closing the scissor jaw sets by retraction, the surgical instrument can be reconfigured such that the clip jaw sets close when rod 26 projects or extends (in a direction opposite retraction) In this embodiment, cam 69 would be positioned at an outboard position (rather than the illustrated inboard position) with respect to common lateral axis 150. Of course, the cam follower channels would be reconfigured to translate forward axial movement into pivotal action of the clip jaw sets and the scissor jaw set.

As shown in FIG. 10, cam 69 is initially positioned on cam initial position axis 151. If protruding movement from rod 26 is utilized, cam axis 151 would be positioned to the right of common lateral pivot axis 150 in FIG. 10. Axis 150 is coextensive with pivot pin 78. The cam following channels would be altered accordingly. The claims appended hereto are meant to cover both retraction of rod 26 as well as protruding action of rod 26.

Further, the illustrated preferred embodiments of the present invention utilize clip carrying jaw sets that have jaw plates defining both upper jaw teeth of end piece 16. Another clip jaw set carries both lower jaw teeth. It should be noted that each jaw tooth could be configured as a single, planar jaw member and each jaw plate or jaw member could have a clip-action cam follower channel therein. In this alternate embodiment (not illustrated), end piece 16 would contain four clip-action cam follower channels rather than the two clip-action cam follower channels 91, 93 illustrated in the figures. The claims appended hereto are meant to cover this alternate embodiment of the present invention.

As shown in the drawings, jaw plates 114, 116 are attached together by base plate 118. Accordingly, these two jaw members of clip jaw set 92 are laterally spaced apart (see space 120 in FIG. 6) and jaw plates 114, 116 pivot conjointly. In a like manner, clip jaw plates 141, 143 are spaced apart laterally and scissor blade 99 fits within that space. Clip jaw plates 141, 143 pivot conjointly about common lateral axis 150.

If four jaw plates are utilized (defining four clip-action cam following channels), each plate would also pivot about the common lateral axis.

Although cam 69 is shown as a pin in the illustrated embodiment, the cam need not be a pin. Cam 69 may be a bar, a triangle, or a nub that laterally protrudes from movable rod 26. One key feature of the present invention is that cam 69 travel within and move the respective back plates of clip jaw sets 90, 92 in scissor jaw members 97, 99 based upon the clip-action cam follower channels 91, 93 and the cut-action cam follower channels 77, 79. Jaw set 90 defines the upper jaw mouth of end piece 16. Set 92 defines the lower jaw mouth.

Although the clip-action cam follower channels 91, 93 are mirror images of each other, those clip-action cam follower channels define substantially the same non-linear cam pathways. They define the same non-linear cam pathways because the upper jaw plates close at substantially the same rate and through substantially the same arcuate distance as the lower clip jaw plates.

The invention described herein also includes the concept of curved cam follower channels. Rather than utilize a broken, two linear segment follower channels, the channels may be curved to provide clip closure at different angular speeds given certain axial rod movements or smoother transitions at the clip closing positions.

The method of the present invention is best shown in connection with FIGS. 4, 10, and 11b-1 through 11e-2. When rod 26 is retracted in a singular operative stroke, cam 69 moves in clip-action cam follower channels 91, 93 and simultaneously closes the upper and lower clip jaw sets 90, 92. This results in a clip-action in lateral jaw areas 51, 55 of FIG. 4 and the collapse and closure of surgical clips 56 and 58 about a blood vessel segment spanned by region A in FIG. 4. The segment may be a segment of blood vessel (artery or vein) or a segment of an organic structure in a body. In any event, due to the high angular offset of clip-action cam follower channels 91, 93 (this angular offset is compared to the axial center line 170 in FIG. 10), the clip jaw sets close prior to the closure of scissor jaw members 97, 99. When cam 69 (starting at initial axis 151, FIG. 10) reaches the first breakpoint in the non-linear clip-action cam follower channels 91, 93 (discussed later), the cam then activates the scissor jaw members 97, 99. The scissor jaw members then close because cut-action cam following channels 77, 79 are not linearly discontinuous (compared to the clip-action channels) at that specified longitudinal position of the cam actuator 69. Accordingly, region 53 (FIG. 4) subsequently closes after clips 56, 58 are collapsed and stapled on a blood vessel segment in region A (FIG. 4).

The method simultaneously clips both sides of segment region A of the blood vessel or other organic structure with two surgical clips 56, 58 during an initial portion of the singular operative stroke and rod retraction based on longitudinal movement of rod 26. Subsequent thereto, rod 26 continues to retract thereby closing scissor members 97, 99 due to the initial linear portion defined by cut-action cam follower channels 77, 79 (FIG. 10), as compared to the initial portion of clip-action cam follower channels 91, 93. The subsequent cutting of segment A of the blood vessel or other organic structure is conducted based upon the singular operative stroke and rod retraction of rod 26. The simultaneous collapse and staple of the U-shaped clips 56, 58 onto the blood vessel is accomplished in a single, generally uniform retraction of rod 26 caused by the operator depressing or compressing handle 12 and particularly moving movable handle member 20 towards stationary handle 22. Handle 12 is diagramatically illustrated in FIG. 1. End piece 16 translates the singular rod retraction movement of rod 26 into sequential pivotal movements of clip jaws in region 51, 55 about a common axis 50 (see FIG. 4). Subsequent thereto, further rod retraction is converted into pivotal action of the scissor jaws and the cutting of the blood vessel.

FIGS. 11b-1 through 11e-2 diagrammatically illustrate the method in accordance with the principles of the present invention. Due to the number of components and the detail of end piece 16, only major components or jaw segments or regions 51, 53 and 55 are diagrammatically illustrated in FIGS. 11b-2, 11c-2, 11d-2 and 11e-2. The sequential method is diagrammatically illustrated by viewing side elevational view of end piece 16 in FIG. 11b-1 generally concurrently with the front elevational view of end piece 16 diagrammatically illustrated in FIG. 11b-2. The method progresses by viewing FIGS. 11b-1; 11c-1; 11d-1 and 11e-1. Front end sequential views are generally shown in FIGS. 11b-2; 11c-2; 11d-2 and 11e-2.

Blood vessel or other organic structure 9 is shown in FIGS. 11b-1 and 11b-2. End piece 16 spans segment A of blood vessel 9. It should be appreciated that blood vessel 9 is illustrated herein because it is difficult to illustrate different types of organic structure which can be first clipped and then cut by the surgical instrument described herein. In FIGS. 11b-1 and 11b-2, end piece 16 is fully open. Left jaw region 51 and right jaw region 55 is in a fully open position as is scissor jaw region 53. Clips 56, 58 are illustrated in FIG. 11b-2. Also, cam 69 is in its initial position which is close to pivot point or common axis 78 as shown in FIG. 11b-1.

Figures 1, 11D:
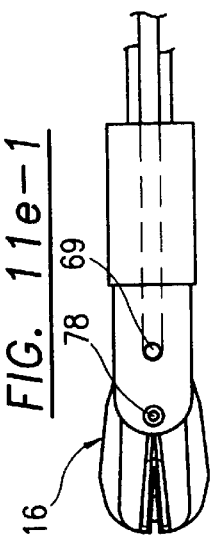
Figures 2, 11D:
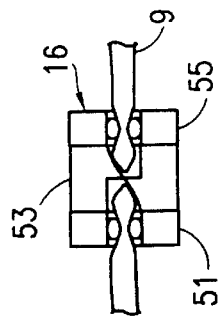
Figures 1, 11C:
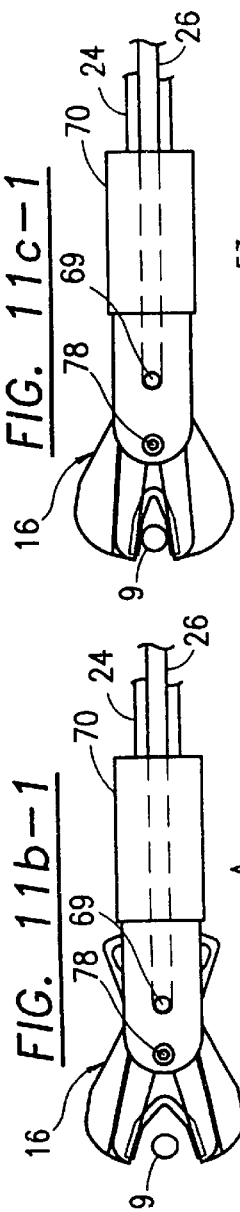
Figures 2, 11C:
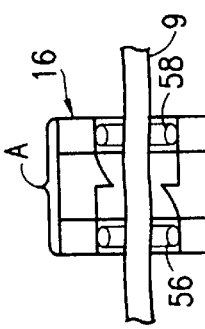

In FIGS. 11c-1 and 11c-2, rod 26 has been slightly retracted, thereby changing the longitudinal position of cam 69 with respect to common lateral axis or pivot point 78. This results in the partial closure of the clip jaw sets as shown by the smaller size of the jaw mouths about jaw regions 51, 55. Scissor jaw set in region 53 has not been fully closed on blood vessel 9. Dependent upon the angular offset of the cut-action cam follower channel, scissor jaw region 53 will remain in its initial position or will begin closing at a rate slower than the clip carrying jaw sets. As shown in FIG. 11c-2, jaw regions 51, 55 are closing faster than scissor jaw region 53.

In FIGS. 11d-1 and 11d-2, the clips have been fully collapsed onto blood vessel 9 and the clip carrying jaw regions 51, 55 are diagrammatically illustrated in a closed or fully collapsed position. This greatly reduces and most likely eliminates fluid flow through the blood vessel. FIG. 11d-2 clearly illustrates that the scissor jaw region 53 remains relatively open as compared with the collapsed or fully clipped on aspect of clip carrying jaw regions 51, 55. The relative dimensions and size of various components illustrated in FIGS. 11b-1 through 11e-2 are not to scale.

Figures 1, 11E:
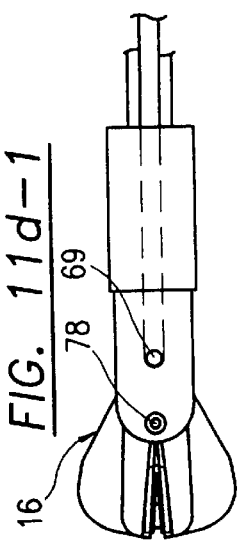
Figures 2, 11E:
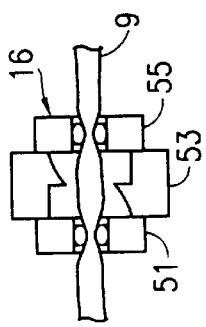

In FIGS. 11e-1 and 11e-2, the scissor jaw region 53 has been fully closed, thereby cutting blood vessel 9. Cam 69 (FIG.11e-1) is far removed from pivot point or common lateral axis 78. This is the final position of cam 69 in relation to the common lateral axis 78.

FIGS. 12 and 13 show upper scissor blade 99 with a wedge shaped blade edge 172, a hole or passageway 78a for pivot pin 78 and a cut-action cam follower channel 79. As shown in FIG. 13, the blade portion 100 of scissor jaw member 99 is wider, e.g., dimension 101, then the width of the backplate 103 which defines the cut-action cam follower channel.

FIGS. 14–16 show upper jaw set 90. Upper jaw set 90 includes jaw plate 141, jaw plate 143, baseplate 145 and backplate 147. Backplate 147 defines a clip-action cam follower channel 91. Clip-action cam follower channel 91 includes an initial linear region 181 which is activated by the cam at substantially the same time as initial linear region 182 of cut-action cam follower channel 79 in FIG. 12. However, initial linear region 182 of cut-action cam follower channel 79 defines a longer initial linear segment and a channel rather than define a smaller angular offset from the axial centerline established by the movable rod. Since the length of channel segment 182 is longer than the length of channel segment 181, and since the angular offset of channel segment 181 is greater than the angular offset of channel segment 182 (with respect to axial centerline 170 in FIG. 10), jaw set 90 closes prior to closure of scissor jaw member 99. Secondary or subsequent channel segment 183 in clip-action cam follower channel 91 simply maintains the closure of the collapsed surgical clips on the blood vessel or organic structure. Secondary linear channel segment 184 of cut-action cam follower channel 79 ensures that the scissors entirely cut through the blood vessel or organic structure.

FIG. 16 diagrammatically shows clip retention channel 190 for clip plate 141 and clip retention channel 192 for clip plate 143. Base plate or member 145 supports the clip plates. Clip jaw plates 141, 143 are spaced apart and this spacing is identified in FIG. 15 as space 194. Upper scissor plate 99 is disposed in space 194 such that the clip jaw plates 141, 143 are disposed on either side of the scissor blade.

FIG. 4 diagrammatically shows that clip jaw sets are composed of multiple plates that are attached together to form a singular unit. For example, in region 55, the lower clip jaw plate includes plate members 201, 202 and 203. These plates are mounted together by an appropriate mechanism. This mechanism may include threaded bolts or other types of attachment (i.e., rivets, weld points, adhesives). At region 53, scissor jaws are defined by two members.

FIGS. 17–20 diagrammatically illustrate the surgical clips. As shown in FIG. 17, surgical clip 301 is generally U-shaped. The clips have a clip face 302 and terminal facial segments 304, 306. Clip 301 has intermediate facial segments 308, 310. Clip 301 is bent in region 312. Facial segments 304, 306, 308 and 310 are generally planar, that is, the clip portions that interface with the blood vessel are primarily planar except for the triangular or V-shaped channels cut or formed therein. Terminal planar facial segment 306 is shown in FIG. 18. The clip face 302 includes a longitudinal center channel 320 which has a triangular or V-shaped cross-section. The triangular cross-section of center channel 320 is shown in FIG. 20. FIG. 20 is a cross-sectional view of clip 301 from the perspective of section line 20'–20" in FIG. 17. The longitudinal center channel 320 extends through all of the planar facial segments 304, 306, 308 and 310.

In FIG. 18, terminal planar facial segment 306 includes an X-shaped channel 322. The vertices of this X-shaped channel 322 are coextensive with the longitudinal center channel 320.

In FIG. 19, terminal planar facial segment 306 includes a first and a second X-shaped channel 322, 324. The legs of the X-shaped channel are angularly disposed at approximately 120°. The X-shaped channels have a triangular cross-sectional shape as shown at channel end segments 340, 341 on clip 301 shown in FIG. 18.

Clip 301 includes a chamfer 342, 344 at its outer, opposing, lateral edges.

In a preferred embodiment, the clips are constructed in three sizes, small, medium and large. The legs of the clip are not parallel but are abducted to fit a clip holder shown in FIGS. 21–22. The X-shaped channels on the terminal planar facial segments and the longitudinal center channel provide a tire grip providing high traction for the clip on the blood vessel or organic structure. The lines of this X-shaped pattern with its coextensive vertices along the longitudinal center channel provide depressions in bas relief on the active clip faces which increase the frictional grip of the clip on the blood vessel from all angles.

The following Exemplary Jaw Dimension Table and Exemplary Clip Dimension Table provide size and dimensional relationship examples for one embodiment of the present invention.

| Exemplary Jaw Dimension Table | |
|---|---|
| length | 0.46 inches |
| width single jaw set | 0.17 |
| width jaw member | 0.1 |
| Exemplary Clip Dimension Table | |
| depth triangular channel | 0.004 inches |
| clip width | 0.03 |
| d to first vertex (from clip end) | 0.045 |
| d to second vertex | 0.120 |
| chamfer | 0.06 |
| overall width (span of U-shape) | 0.24 |
| major angle | 37° |
| length | 0.2 |

The clips are constructed of titanium or tantalum. The clips are also designed with a greater angle to the diverging leg segments defining terminal planar facial segments 304, 306, in order to fit the end piece 16 tightly.

With respect to FIGS. 21 and 22, clip holders 501 retain three pair of surgical clips. One clip is mounted in space 502 and the second clip is mounted in space 504. The next pair of clips are mounted in region 506 and the third pair of clips is mounted in region 508. Clips are disposed and spaced apart by separating bracket 509 shown in FIG. 22.

Clip holder 501 is designed and packaged to be a single sterilizable package. The interior of the package and its contents are sterilized using ethylene oxide gas or gamma radiation. The packages are dated to ensure sterility. The package is opened aseptically and clips are transferred to the sterilized clipping instrument, end piece 16, by sliding the jaws of the end piece 16 into the channel of the holder and removing two perfectly aligned clipped simultaneously.

Clip holder 101 is approximately one inch or less in length. It is made of thermoplastic material or stamped material. The holder is shaped to contain metal hemostatic or marking clips in perfect alignment for transfer to end piece 16, the crimping or clipping instrument. The size of clip tray 501 is optimum to be held between the thumb and the forefinger of the user. The shape of the core 503 and notches 531, 532 are positioned in size to hold two or more clips in perfect alignment prior to transfer to the end piece 16. The clips are held in place by small notches or nubs, two of which are illustrated as notches 531, 532 and clip space 504.

Figure 23:
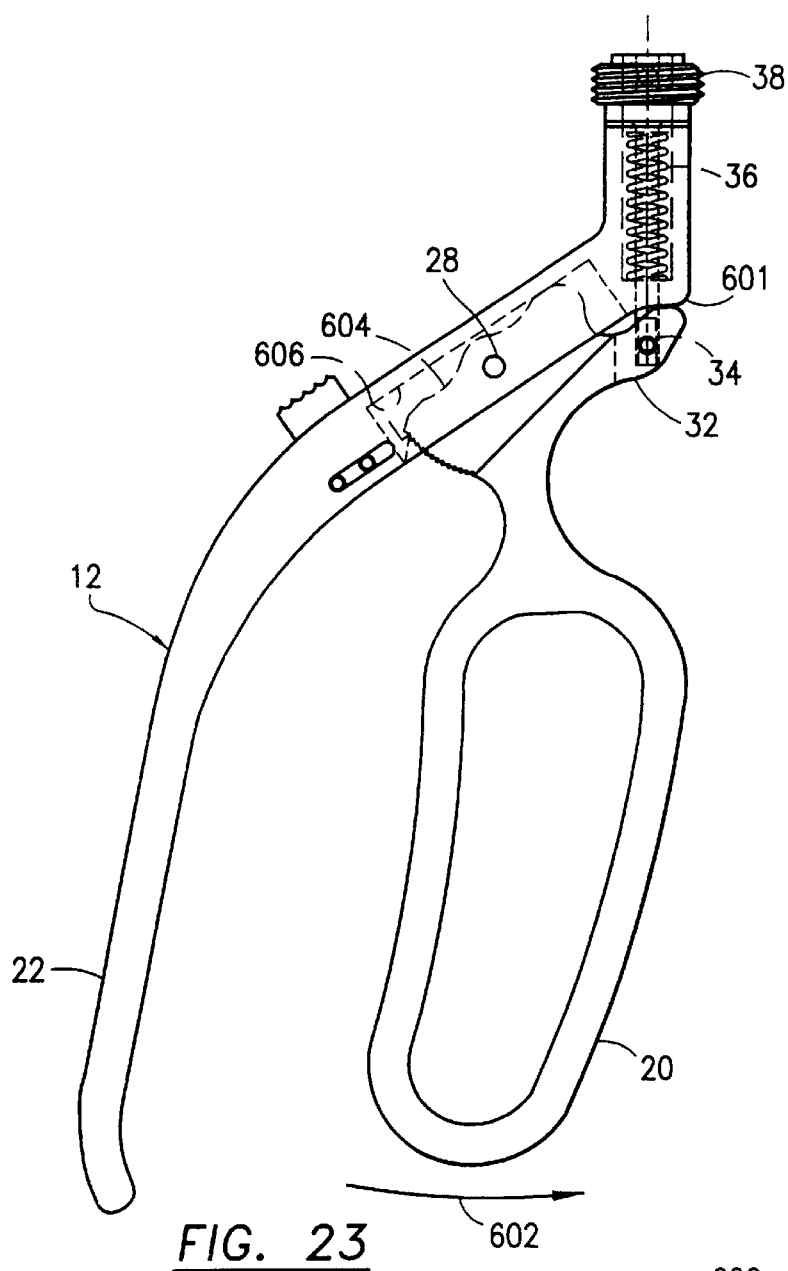
FIG. 23 diagramatically illustrates a handle for the surgical instrument and one type of tactile response surface.

FIG. 23 diagrammatically illustrates handle 12. Handle 12 includes stationary grip member 22 and movable handle member 20. Movable member 20 is pivotally mounted to stationary member 22 via pivot pin or bolt 28. Stem 32 of movable member 20 is movably coupled to an actuator rod 34. Stem 32 is biased towards handle stop 601 due to biasing spring 36. Of course, other biasing mechanisms could be utilized such as leaf spring and pneumatic or hydraulic springs or mechanisms. In this manner, movable handle member 20 is biased in the "full open" direction shown by arrow 602.

Movable handle 20 includes a tactile response surface 604. In the illustrated embodiment, tactile response surface 604 is an undulated or wavy surface. Other types of tactile response surfaces could be utilized such as the fine tooth tactile surface shown in connection with FIG. 26. Tactile surface 604 could be a plurality of nubs or protrusions which ride on and bump against tactile response wall 606 of stationary handle member 22.

Figure 24:
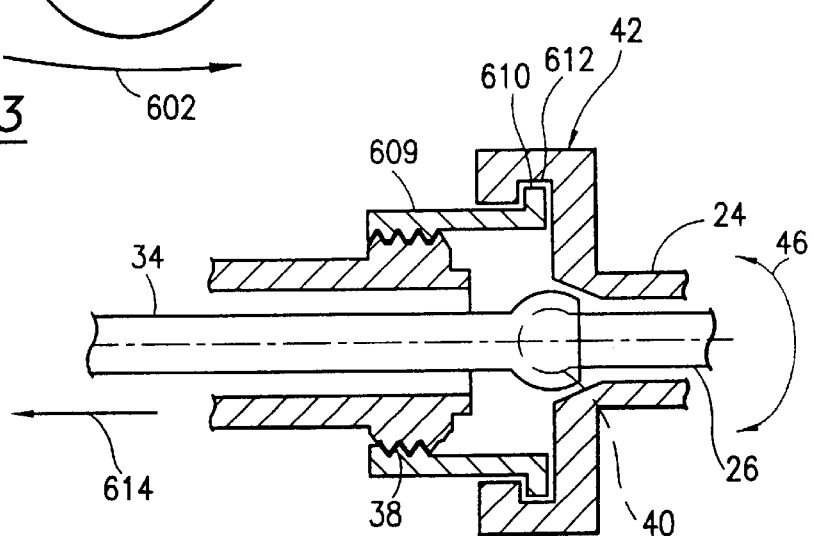
FIG. 24 diagramatically illustrates the coupling between a handle actuator member and the longitudinally movable rod, and particularly shows the ability of the operator to rotate the elongated tube thereby rotating the attached end piece.

FIG. 24 diagrammatically illustrates details of the coupler section between handle 12 and the elongated tube 24 as well as the movable rod 26. Inboard handle segment has a male threaded joint 38 which threads onto a female threaded section 609. Female threaded section, at its inboard side, includes a rotatable coupling illustrated, in this embodiment, as a radially protruding ridge 610. Outer rotating coupling 42 forms a channel 612 within which is captured radially extending ridge 610. In this manner, the user can rotate female rotating unit 42 relative to male rotating coupler 610 as shown by the double headed arrow 46. This rotation in direction 46 rotates the elongated tube 24 and therefore rotates end piece 16 (see FIGS. 1 and 2).

Actuator rod 34, in this illustrated embodiment, includes a ball and socket joint within which ball 40 of movable rod 26 is placed. In this manner, when actuator 34 is retracted as shown by arrow 614, rod 26 is also retracted. The dimensions and the sizing of various components in FIG. 24 do not reflect actual size or dimensional relationships of the components. For example, movable rod 26 may be closely captured by tube 24. In this manner, rod 26 may have various types of cross-sectional configurations. However, the ability of the operator to rotate end piece 16 by rotating female coupler 42 may be affected by the cross-sectional configuration of rod 26.

In operation, when the operator compresses handle 20 towards stationary handle 22 (a direction opposite arrow 602), the user feels tactile response surface 604 as it bumps against response wall 606. Response wall 606 is defined in the stationary handle member 22. This informs the operator via tactile sensation that rod 26 has retracted to a certain linear position which may be compressed to first clip or close the blood vessel before cutting the blood vessel.

FIG. 25 diagrammatically illustrates a handle 12 for a surgical instrument. Handle 12 includes stationary grip member 22 and movable member 20. Movable member 20 is pivotally attached at pivot point 702 to stationary grip member 22. Handle 12 includes an operator control surface 704 which is explained in greater detail in FIGS. 26 and 27.

Handle 12 in FIG. 26 includes a movable member 20 having a tactile response surface 706 consisting of a plurality of fine teeth. Tactile response surface 706 abuts a responsive tactile piece 708 movably mounted in stationary grip member 22. Responsive tactile piece 708 is biased in the direction shown by arrow 709 towards tactile response surface 706. Spring 710 biases responsive tactile piece 708 towards tactile response surface 706. Other types of biasing mechanisms could be used such as leaf springs, U-shaped spring pieces, pneumatic and hydraulic springs. Also, responsive tactile piece 708 may be loosely mounted in stationary grip member 22 such that when movable handle member 20 is compressed or moved toward stationary handle member 22, responsive tactile piece 708 "jumps" or generates tactile and/or audible clicks every time a tooth or a ridge on tactile response surface 706 passes complementary fine tooth point 712 on tactile response piece 708. Piece 708 in the illustrated embodiment is a movable block.

In the illustrated environment, spring 710 biases responsive tactile piece 708 towards tactile response surface 706. Tactile response piece 708 includes an operator control surface 704 which permits the operator to move response piece 708 rearward in the direction shown by arrow 714. This operator input counters the forward bias of the piece 78. The control surface is exposed to the operator and rises above handle member 22. By moving response piece 708 in the direction shown by arrow 704, complementary fine tooth detector 712 is moved away from tactile response surface 706 thereby eliminating any tactile response (or other response) based upon the compression of movable handle piece 20 towards stationary grip member 22. It should be remembered that when movable handle member 20 is compressed towards stationary grip member 22, actuator piece 34 retracts and further retracts rod 26, thereby closing the clip and subsequently closing the scissor jaws.

In the embodiment illustrated in FIG. 26, complementary fine tooth 712 on responsive tactile piece 708 and fine tooth ridges establishing tactile response surface 706 provide a ratchet set. Complementary fine tooth 712 has a 90° lagging tooth angle prohibiting movable handle member 20 to move outboard away from stationary handle member 22 when the ratchet is actuated. The other slope or leading edge of complementary fine tooth 712 is generally complementary to the leading angle of the plurality of fine tooth ridges on tactile response surface 706 such that movable handle member 20 can be compressed towards stationary grip member 22 without serious locking or latching of the complementary fine tooth 712 on the plurality of fine tooth ridges 704, 706.

Responsive tactile piece 708 also includes a latch or a lock as shown in FIG. 27 such that the operator can lock responsive tactile piece 708 in an OFF position. This latch is provided by detent 720 which captures a complementary nub 722 upon full rearward retraction of piece 708 away from teeth 706. In addition, nub 722 provides a guide pin along with pin 724 to guide the responsive tactile piece 708 backwards and forwards in accordance with operator demands. In another embodiment, the latch may be configured at other points of travel of piece 708 in handle member 22.

It should be appreciated that the present invention includes a configuration where the responsive tactile piece is mounted to the movable handle and the tactile response surface is configured on the stationary grip. The mechanical reversal of these components is easily accomplished, i.e., the tactile piece may be mounted on stationary handle member 20 and the response surface defined on movable member 22. The claims appended hereto are meant to cover this configuration.

The claims appended hereto are meant to cover modifications and changes within the scope and spirit of the present invention.

What is claimed is:

1. A surgical staple clip for closure of a blood vessel or other organic structure comprising a clip body having a clip face adapted to interface with said blood vessel or other organic structure, said clip face having planar facial segments and a longitudinal center channel with a triangle cross-section there through, a terminal planar facial segment defines an X-shaped channel with a vertex co-extensive with said longitudinal center channel, said X-shaped channel having a triangular cross-section.

2. A surgical staple clip as claimed in claim 1 including two X-shaped channels, with vertices co-extensive with said longitudinal center channel, on each terminal planar facial segment.

3. A surgical staple clip as claimed in claim 2 wherein said clip face has a chamfer along its outer, opposing edges.

4. A surgical staple clip as claimed in claim 3 wherein said terminal planar facial segments are disposed at opposing ends of said clip face and said clip face includes intermediate planar facial segments and a medial bend segment.

* * * * *